(12) United States Patent  
Sinkus et al.

(10) Patent No.: US 7,025,253 B2  
(45) Date of Patent: Apr. 11, 2006

(54) METHOD OF EXAMINING AN OBJECT BY MEANS OF ELASTOGRAPHY

(75) Inventors: Ralph Sinkus, Hamburg (DE); Steffen Weiss, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/506,456

(22) PCT Filed: Feb. 26, 2003

(86) PCT No.: PCT/IB03/00757

§ 371 (c)(1),  
(2), (4) Date: Aug. 31, 2004

(87) PCT Pub. No.: WO03/073933

PCT Pub. Date: Sep. 12, 2003

(65) Prior Publication Data

US 2005/0104588 A1    May 19, 2005

(30) Foreign Application Priority Data

Mar. 1, 2002    (DE) ................................. 102 09 257

(51) Int. Cl.  
*G01V 3/00*    (2006.01)

(52) U.S. Cl. ...................................... 234/309; 324/307

(58) Field of Classification Search .................. 324/309, 324/307, 318, 319, 322, 300; 600/410  
See application file for complete search history.

(56) References Cited

U.S. PATENT DOCUMENTS

| | | | | |
|---|---|---|---|---|
| 5,825,186 | A * | 10/1998 | Ehman et al. | 324/309 |
| 5,899,858 | A * | 5/1999 | Muthupillai et al. | 600/410 |
| 6,246,895 | B1 | 6/2001 | Plewes | |
| 6,486,669 | B1 | 11/2002 | Sinkus et al. | |
| 6,636,756 | B1 * | 10/2003 | Zhu | 600/410 |
| 6,833,703 | B1 * | 12/2004 | Sinkus et al. | 324/318 |
| 6,862,468 | B1 * | 3/2005 | Smith | 600/410 |
| 6,879,155 | B1 * | 4/2005 | Ehman et al. | 324/309 |
| 6,897,653 | B1 * | 5/2005 | Van Den Brink et al. | 324/307 |
| 2003/0128033 | A1 * | 7/2003 | Sinkus et al. | 324/318 |

FOREIGN PATENT DOCUMENTS

EP    0 708 340 A1    4/1996

\* cited by examiner

*Primary Examiner*—Brij B. Shrivastav  
(74) *Attorney, Agent, or Firm*—Thomas M. Lundin

(57) ABSTRACT

In a method of elastography, diagnostic performance is improved in that the variation in time of the excursion whereby a region responds to excitation by mechanical oscillations is analyzed and the non-linear distortions are measured. Such non-linear distortions are a measure of the non-linear elastic properties of the region and constitute a diagnostically relevant item of information.

14 Claims, 4 Drawing Sheets

METHOD OF EXAMINING AN OBJECT BY MEANS OF ELASTOGRAPHY

BACKGROUND

The invention relates to a method of examining an object by means of elastography, as well as to an arrangement for carrying out such a method and to a computer program for controlling such an arrangement.

The MR elastography (MR=Magnetic Resonance) method which is disclosed in U.S. Pat. No. 6,486,669 utilizes the fact that the phase in an MR image of the object changes under the influence of mechanical oscillations acting on the object. The extent of such a change is dependent on the excursion of the. tissue under the influence of the mechanical oscillations. Information concerning given mechanical parameters of the tissue can thus be derived from MR phase images, that is, images reproducing the phase of the nuclear magnetization; for example, such a parameters relates to the elasticity. In ultrasound elastography even direct measurement of the excursion is possible.

Malignant lesions such as, for example, a mastocarcinoma, clearly deviate in respect of elasticity from normal healthy tissue. However, there are also benign lesions which have similar elastic properties. Anomalous elastic properties, therefore, per se do not yet form an adequate indication that a tissue is malignant.

SUMMARY

It is an object of the present invention to provide a method of elastography such that additional information is derived which enables better differentiation between different types of tissue. This object is achieved by means of a method for examining an object in accordance with the invention which includes the steps of:

a) exciting the object by means of mechanical oscillations, b) measuring the variation in time of the excursion from the rest state of voxels of the object which are subject to the waves caused by the oscillations in the object, c) determining the non-linear distortions from the variation in time of the excursion, and d) evaluating the non-linear distortions.

The invention is based on the following considerations and insights. When a pressure exerted on biological tissue is varied, the deformation of the tissue does not vary to the same extent as the pressure, because the modulus of elasticity increases (the tissue becomes harder). This non-linear relationship between pressure and deformation is particularly pronounced in the case of malignant lesions and is the reason why, when the tissue is excited by mechanical oscillations, the variation in time of the excursion no longer corresponds to the variation in time of the mechanical oscillations but exhibits (non-linear) distortions. Therefore, the non-linear distortions in the temporal variation of the excursion of a voxel are a measure of the non-linearity; such a measure is suitable for the classification of tissue. In the case of excitation by means of, for example, mechanical oscillations which vary sinusoidally in time, such distortions cause the excursion of the voxels in the object to be no longer purely sinusoidal and that it additionally exhibits higher harmonics of the mechanical oscillations, notably harmonics of twice the frequency.

Each voxel could be individually measured so as to determine the non-linear distortions (and possibly also the elasticity) measured for each voxel. The version disclosed in claim 2, however, makes it easier for the examiner to form a diagnosis for a larger region.

Claim 3 enables the invention to be carried out by means of MR elastography means, thus enabling location-dependent determination of the modulus of elasticity in addition to the non-linearity. In principle, however, the method can also be carried out by means of ultrasound.

Claim 4 discloses a version of the method of claim 3 which enables the simultaneous measurement of excursions of a voxel at the fundamental frequency and at twice the fundamental frequency. Instead, however, it would also be possible to compose the magnetic gradient field from a component having the fundamental frequency and a component having twice the fundamental frequency.

The further version as disclosed in claim 5 prevents field inhomogeneities from exerting a disturbing effect on the phases. In this case the two individual sinusoidal oscillations of the gradient field must have the same phase position.

The version disclosed in claim 6 takes into account the fact that the (location-dependent) non-linearity and elasticity tissue enable improved classification of the tissue. The method disclosed in claim 3, however, does not require additional measurements for this purpose.

Claim 7 defines an MR apparatus for carrying out the method in accordance with the invention and claim 8 discloses a computer program for controlling an MR apparatus of this kind.

BRIEF DESCRIPTION OF THE DRAWINGS

The invention may take form in various components and arrangements of components, and in various steps and arrangements of steps. The drawings are only for purposes of illustrating the preferred embodiments and are not to be constructed as limiting the invention.

DETAILED DESCRIPTION

The following known relation exists between the pressure P on a sample and the deformation $\epsilon$ of the sample due to this pressure:

$$P = \epsilon E \qquad (1)$$

Therein, E is the elasticity of the tissue. For the deformation $\epsilon$ it holds that:

$$\epsilon = (L_0 - L)/L_0 \qquad (2)$$

Therein, $L_0$ is the extent of the non-compressed sample and L the extent of the compressed sample. As has already been stated, in the case of samples of a biological tissue the deformation $\epsilon$ is not proportional to the pressure P, because the elasticity increases as the deformation increases. This increase can be suitably approximated by the equation $$E = E_0 e^{\alpha \epsilon} \qquad (3)$$

Therein, $E_0$ is the is the initial elasticity (that is, the elasticity without compression) and the exponent α is a measure of the non-linearity. For α=0 a linear relationship exists between P and ε. The larger α, the more non-linear this relationship will be.

Figure 1:
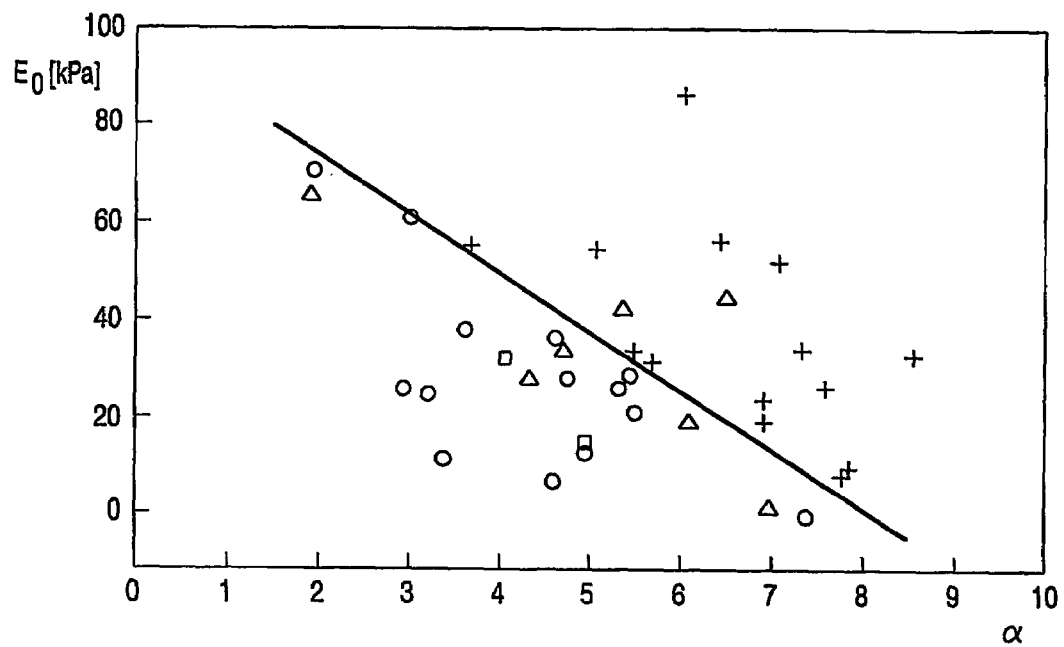
FIG. 1 shows a diagram for the classification of different types of tissue.

FIG. 1 shows a diagram in which the elasticity $E_0$ is plotted as the ordinate and the exponent α, characterizing the non-linearity, is plotted as the abscissa. With each sample in FIG. 1 there can be associated a point which characterizes the elasticity $E_0$ and the exponent α for this sample. In the diagram a number of tissue samples are marked by a respective symbol. The symbol "+" denotes tissue samples from a mastocarcinoma. The symbol "□" denotes benign lesions in the form of a fibroadenoma, the symbol "¤" denotes fat tissue and the symbol "Δ" denotes tissue samples of growths in the milk ducts which could change from a benign to a malignant condition.

Tissue samples of mastocarcinomas have a higher elasticity (i.e. they are harder) and at the same time a more pronounced non-linear relationship between the pressure P and the deformation s in comparison with healthy tissue. Therefore, tissue samples can be classified on the basis of these parameters. Tissue samples situated to the right of the straight line in the diagram are indicative of a malignant lesion whereas tissue samples situated to the left thereof are indicative of a benign lesion.

The diagram of FIG. 1 is based on in vitro examinations of tissue samples during which the tissue samples were exposed to an increasing pressure P and the deformation ε was measured. The examination of tissue of living patients in this manner is not without difficulty. The invention is based on the recognition of the fact that the same parameters can be non-invasively determined for living patients while utilizing elastography means. When a living object is excited by stationary mechanical oscillations, the excursion of the voxels in the mechanical tissue should exhibit the same variation in time as the mechanical oscillations if the elasticity were constant and independent from the deformation. However, when a voxel is situated within a tissue which exhibits a non-linear relationship between the pressure P and the deformation ε, the excursion of the voxel can no longer exactly follow the variation in time of the oscillations and distortions occur which are a measure of the non-linearity. The measurement of these distortions or non-linearity will be described in detail hereinafter on the basis of an example involving MR elastography.

Figure 2:
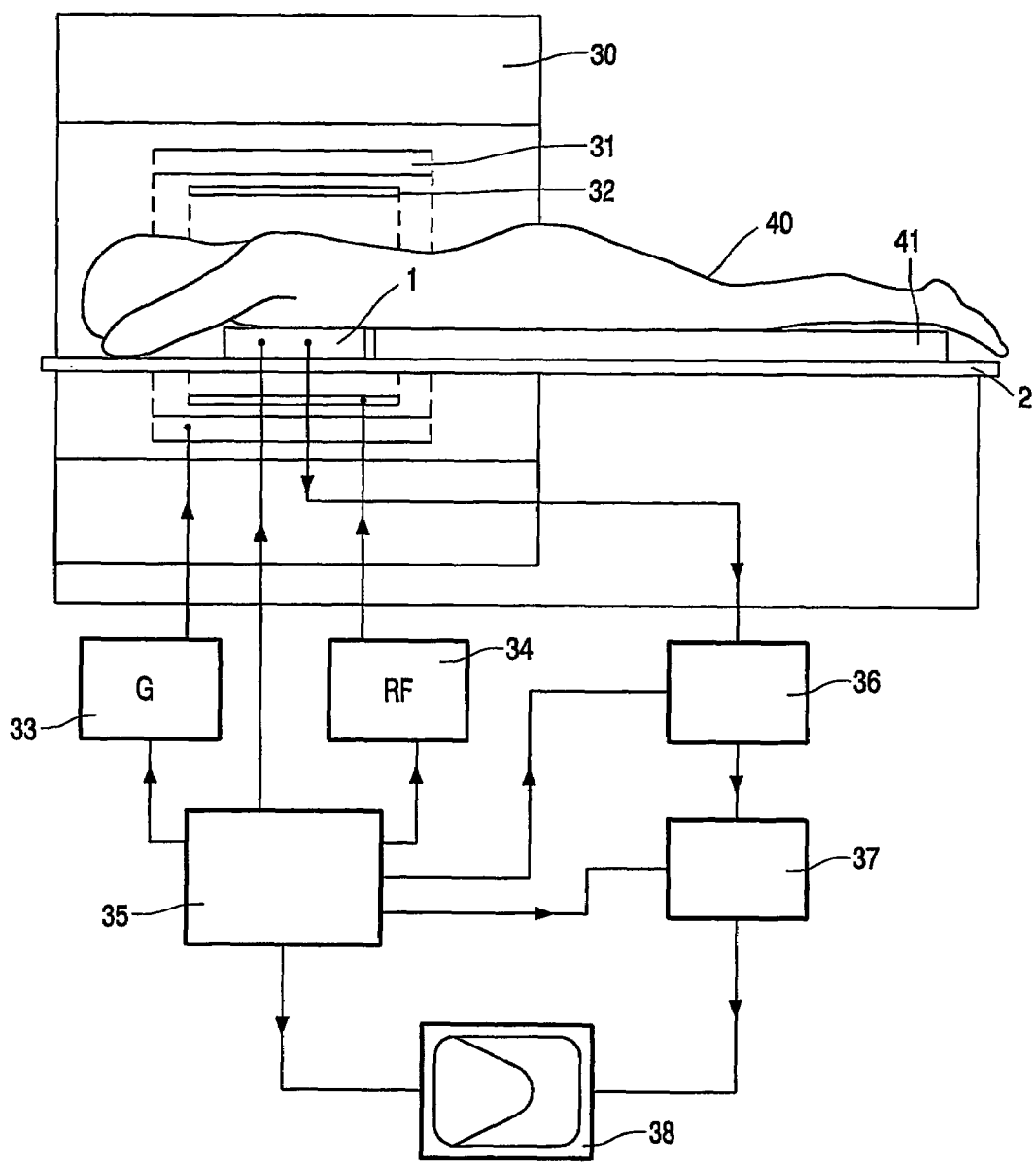
FIG. 2 shows an MR apparatus for carrying out the method in accordance with the invention.

FIG. 2 is a diagrammatic sectional view of an MR apparatus for carrying out this method and also shows the hardware and software components required for the operation thereof. The MR apparatus includes a main field magnet 30 for generating a main magnetic field $B_0$ which extends horizontally and parallel to the plane of drawing of FIG. 2. Inside this cylindrical main field magnet there is arranged a set 31 of gradient coils which serve to generate magnetic fields having gradients in three mutually perpendicular directions. Inside these gradient coils there is arranged an RF coil 32 for generating an RF magnetic field.

The currents for the gradient coils 31 are supplied by a generator arrangement 33 whereas the currents for the RF coil 32 are supplied by an RF generator 34. The variation in time of the currents generated by the generators 33 and 34 is determined and controlled by a control unit 35. The MR signals generated in the mammae during the examination are received by MR coils (not shown) so as to be further processed in a receiver 36. The output signals of the receiver 36 are applied to an image processing unit 37 which reconstructs an MR image from the MR signals received; this MR image is displayed on a monitor 38.

In the examination zone defined by the coils 31 and 32 there is arranged a female patient 47 who is positioned on a cushion 41 resting on a patient table 2. In front of the cushion 41 there is arranged a mammography accessory 1 which has the same height as the cushion 41. The mammae of the patient hang down in openings of the mammography accessory in which they are exposed to mechanical oscillations while being slightly compressed, said oscillations propagating in the horizontal direction (from the feet to the head) while varying sinusoidally in time. The variation in time of the mechanical oscillations produced in the mammography accessory 1 are synchronized, by means of the control unit 35, with the variation in time of the currents generated by the generators 33 and 34.

The above MR apparatus is described in detail in German patent application 10156178.4 (PHDE 010302) whereto reference is made in order to avoid duplication.

Figure 3:
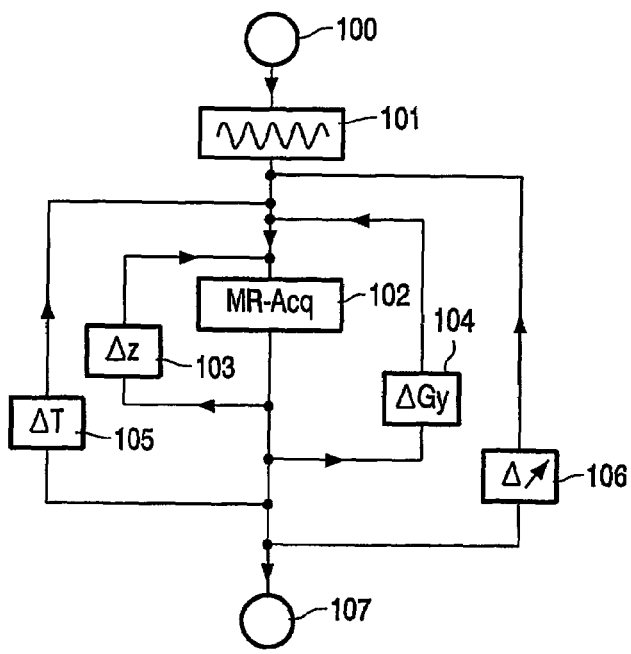
FIG. 3 shows a flow chart illustrating the acquisition of MR phase images.

FIG. 3 illustrates the execution in time of the acquisition of the MR data for an MR elastography examination by means of the MR apparatus shown in FIG. 2. After the completion of the initialization (100) and after the patient 40 has been positioned in conformity with FIG. 1, the mammae of the patient are slightly compressed so that they are fixed and still elastically deformable. Subsequently, mechanical oscillations which vary sinusoidally in time are generated in the mammography accessory 1, said oscillations acting on the mammae of the patient and lasting for the entire MR acquisition (block 101).

Figure 4:
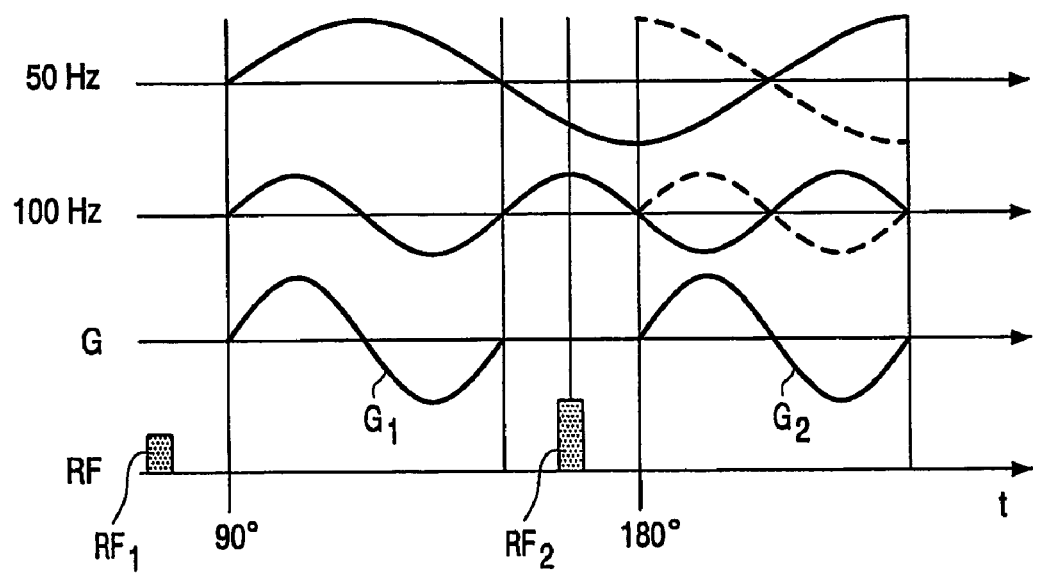
FIG. 4 shows one of the sequences intended for the MR acquisition.

After said oscillations have become stationary, in block 102 there is first generated a first MR sequence whose variation in time is shown in FIG. 4. The sequence comprises a 90° RF pulse $RF_1$ and subsequently a refocusing 180° RF pulse $RF_2$ (fourth line of FIG. 4). Between the two RF pulses $RF_1$ and $RF_2$ there is generated a single, temporally sinusoidally varying oscillation $G_1$ of the magnetic gradient field (third line of FIG. 4); the period duration of this oscillation amounts to exactly half (for example, 10 ms in the case of a frequency of the mechanical oscillation of 50 Hz) of the period duration of the mechanical oscillations. After the second RF pulse, a second oscillation $G_2$ of the magnetic gradient field G is generated; this second oscillation has exactly the same variation in time as the oscillation $G_1$ and its beginning has been shifted by one quarter period (5 ms) of the mechanical oscillation relative to the end of the first oscillation.

During the two RF pulses $RF_1$ and $RF_2$, a magnetic gradient field is applied in the z direction, said gradient field allowing the RF pulses to become active exclusively in a slice extending perpendicularly to the longitudinal direction of the patient; like the phase encoding gradient and the read gradient, this gradient field is not shown either in FIG. 4.

The first line of FIG. 4 shows a part of the variation in time of the mechanical oscillations and the second line shows a higher harmonic of these oscillations at twice the frequency. Such higher harmonics can occur continuously in regions in which a non-linear relationship exists between the deformation and the elasticity when the waves excited by the mechanical oscillations propagate in the mammae and reach such regions. Moreover, the dashed lines of these two first lines indicate that the spins deflected at the relevant frequency are refocused by the pulse $RF_2$.

The gradient oscillations $G_1$ and $G_2$ change the phase of the nuclear spins deflected by the mechanical oscillations. The extent of the change is dependent on the degree of excursion in the direction of the relevant gradient, whereas the sign of the change is dependent on the phase position between the gradient oscillation and the excursion of the nuclear spins.

It appears from FIG. 4 that the sign of the gradient oscillation $G_1$ changes whereas the sign of the mechanical 50 Hz oscillation (first line) remains the same. Therefore, no change of phase occurs. However, the second gradient oscillation $G_2$ causes a change of phase because the 50 Hz oscillation has its zero crossing at the same instant as the gradient oscillation $G_2$. The two gradient oscillations $G_1$ and $G_2$ cause equally large changes of phase for the spins deflected at the harmonic (100 Hz) of the fundamental frequency, said changes being summed because of the variations shown.

The sequence shown in FIG. 4 is sensitive to the excursion at the fundamental frequency as well as to the excursion at twice the fundamental frequency. If this were not the case, the fundamental frequencies of the excursion and their harmonic would have to be separately measured, so that the measuring time would be prolonged.

After the reception of the resultant MR signal in the step 102, the MR sequence is repeated in the step 103 for a different slice which has been shifted in the z direction (extending horizontally in FIG. 2) (block 103). Merely the carrier frequency of the RF pulses $RF_1$ and $RF_2$ is then varied in such a manner that the other slice is excited while the variations in time of the magnetic gradient fields remain the same. The loop comprising the steps 102 and 103 is then repeated as many times as there are slices in the three-dimensional region to be examined, for example, 20 times, each time a different slice being excited.

Subsequently, the phase encoding gradient is changed in the step 104 and all slices are excited again so as to acquire the spin echo signals generated therein. Each individual slice is then excited with the same position in time of the RF pulses and the magnetic gradient fields in relation to the mechanical oscillation. The phase encoding gradient is changed as many times as there are phase encoding steps required, for example, 128 or 256 times. The MR data are thus acquired from all slices so that an MR image can be reconstructed therefrom; this image represents the phase of the nuclear magnetization distribution in the three-dimensional region formed by the slices.

After the acquisition of the MR data for the first MR phase image of the three-dimensional region, in the step 105 a shift in time takes place between the MR sequences and the mechanical oscillations, that is, a shift such that the beginning of an MR experiment is shifted by a fraction of a period $\Delta T$; for example, $\Delta T = T/8$ (step 105). Subsequently, the loop comprising the steps 102, 103 and 104 is completed again so that a further MR phase image of the three-dimensional region being examined is obtained. The two MR phase images differ only in respect of the regions in which the tissue or the nuclear spins excited therein have been deflected in the x direction. After that there are formed further phase images for which the shift in time between the mechanical oscillations and the sequences is changed (for example, $\Delta T = 2T/8, 3T/8 \ldots 7T/8$. The data entered by the user or fetched by the entry made by the user can be displayed on the monitor 8 or also on a separate display.

Finally the MR data of a number of MR phase images (8 in the present example) have been acquired, said MR data being dependent on the excursion of the spins in the x direction, that is, assuming that the gradient of the gradient fields $G_1$, $G_2$ extends in the x direction.

In order to enable measurement of the excursion also in a direction other than the x direction, the sinusoidal gradients $G_1$ and $G_2$ are formed in a direction other than the x direction (block 106), for example, in the y direction, so that, after completion of the loop comprising the steps 102, 103, 104 and 105, there is obtained a set of MR phase images of the three-dimensional region which has been influenced by the excursion of the spins in the y direction. Finally, this procedure is repeated for the z direction (that is, the sinusoidal gradients $G_1$ and $G_2$ are applied in the z direction), so that finally there are available three sets of 8 MR phase images each which are dependent on the excursion of the spins in the x direction, the y direction or the z direction. The acquisition method is then terminated (block 107).

Figure 6:
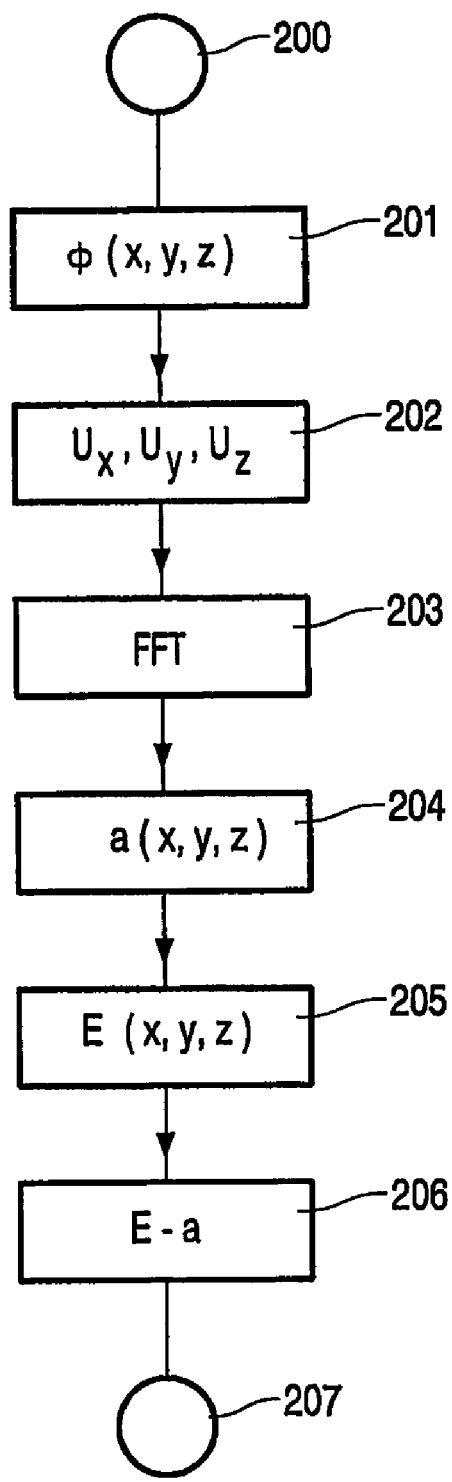
FIG. 6 shows a flow chart of the evaluation process.

The processing of the acquired MR data will be described in detail hereinafter with reference to FIG. 6. As has already been stated, after the initialization in the block 200 MR phase images are formed from the acquired MR data in the step 201. In the step 202 the variation in time of the excursion $u_x$, $u_y$ and $u_z$ is determined for each of the three spatial directions, that is, for the individual voxels of the three-dimensional examination zone.

Figure 5:
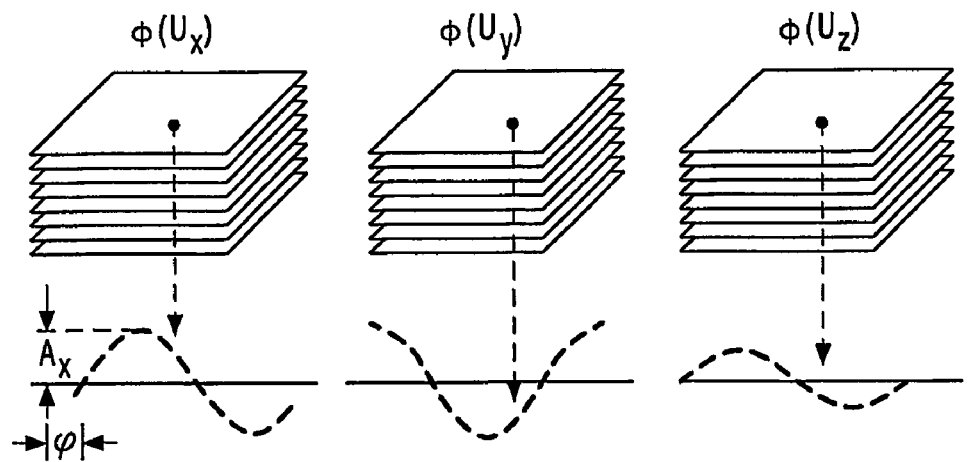
FIG. 5 is a diagrammatic representation of a part of the evaluation process.

For the purpose of illustration reference is made to the diagrammatic representation of FIG. 5. The upper line diagrammatically shows the three sets of MR phase images which are dependent on the excursion in the x direction, the y direction and the z direction, respectively. In each MR image associated with a set the phase is considered in the same voxel. The eight images yield eight base points for the variation in time of the phase or the excursion in the x direction, the y direction or the z direction in the relevant voxel. When this voxel is situated in a region exhibiting non-linear elastic properties, the excursion in this voxel will not be purely sinusoidal in time, because the deflection in this voxel contains, in addition to a component having the frequency of the fundamental oscillation, also higher harmonics, notably a component having twice the fundamental frequency.

In order to determine the amplitude of these components, in the step 203 a Fourier transformation is carried out over the phase or the excursion of the voxel as defined by the eight base points. The Fourier transformation yields three quantities $a_{1x}$, $a_{1y}$ and $a_{1z}$ which represent the amplitudes of the excursion in the x direction, the y direction and the z direction at the fundamental frequency, and also yields three further quantities $a_{2x}$, $a_{2y}$ and $a_{2z}$ which represent the amplitudes of the excursion in the x direction, the y direction and the z direction at double the fundamental frequency. The amplitude $a_1$ of the component having the fundamental frequency can be calculated therefrom in conformity with the equation:

$$a_1 = \sqrt{a_{1x}^2 + a_{1y}^2 + a_{1z}^2} \tag{4}$$

For the amplitude of the component having twice the fundamental frequency it holds that:

$$a_2 = \sqrt{a_{2x}^2 a_{2y}^2 a_{2z}^2} \tag{5}$$

When the two components are related to one another in conformity with the equation $$a = \frac{a_2}{a_1} \tag{6}$$

there will be obtained a value a which is a measure of the non-linearity. Granted, the amplitude $a_2$ per se would already be a measure of the non-linearity, but $a_2$ is dependent not only on the non-linearity but also on the attenuation of the wave produced by the excitation in the object. The parameter a is independent therefrom to a high degree. It corresponds to the value α of the non-linearity in conformity with the equation 3. This correspondence is given via the exact application of the distortion tensor as well as the free energy while taking into account higher terms. The relationship between α and a increases strictly monotonously. Therefore, analogously to FIG. 1, an equivalent diagnostic opinion can be given by way of $E_0$ and a.

After a respective value a has been determined for all voxels, in the step 204 images can be formed which represent the non-linearity of the elasticity in the examination zone.

Because the non-linearity per se generally does not allow an opinion to be expressed as regards the benign or malignant nature of a lesion, as described with reference to FIG. 1, in the step 205 there is furthermore generated an image which represents the spatial distribution of the modulus of elasticity in the examination zone. The measuring values required for this purpose are available already after the acquisition in conformity with FIG. 3. The calculation of the modulus of elasticity from these values is described in detail in the previously mentioned U.S. Pat. No. 6,486,669, which is hereby specifically referred to.

The user can then select individual regions in an image, for example, regions marked by means of a cursor, and be presented with the values of E and a for these regions, for example, in a diagram analogous to FIG. 1 (step 206). The method is then terminated.

As has already been stated, ultrasound elastography means are also suitable for tracking the propagation of the waves excited by the mechanical oscillations in the object, such tracking being significantly faster than in MR elastography. The non-linear distortion of the variation in time, resulting from the non-linear properties of the tissue, can then be determined in a manner analogous to that described above. In addition to the mammae, other regions may also be examined, for example, the prostate.

The invention has been described with reference to the preferred embodiments. Modifications and alterations may occur to others upon reading and understanding the preceding detailed description. It is intended tat the invention be constructed as including all such modifications and alterations insofar as they come within the scope of the appended claims or the equivalents thereof.

The invention claimed is:

1. A method for examining an object, which method includes:
   a) exciting the object by means of mechanical oscillations;
   b) measuring the variation in time of the excursion from the rest state of voxels of the object which are subject to the waves caused by the oscillations in the object;
   c) determining a measure of the non-linear distortions from the variation in time of the excursion;
   d) evaluating the non-linear distortions; and
   e) reconstructing an image representing the extent of the non-linear distortions.

2. A method for examining an object, which method includes the steps of:
   a) exciting the object by means of mechanical oscillations,
   b) measuring the variation in lime of the excursion from the rest state of voxels of the object which are subject to the waves caused by the oscillations in the object,
   c) determining the non-linear distortions from the variation in time of the excursion, and
   d) evaluating the non-linear distortions.

3. A method as claimed in claim 2, which method includes the steps of:
   a) exciting the object in an examination zone by means of temporally periodically, preferably sinusoidally varying mechanical oscillations,
   b) exciting the nuclear magnetization in the object in the examination zone in conjunction with a magnetic gradient field (G1, G2) which is synchronous with the mechanical oscillations, and receiving the MR signals arising in the object in order to form an MR phase image, the variation in time of the gradient field being chosen to be such that the MR signals are determined by excursions at the fundamental frequency as well as by excursions at at least one higher harmonic of the fundamental frequency,
   c) repeating the step b) a number of times while varying the direction of the gradient of the gradient field and/or the phase difference between the mechanical oscillations and the gradient field in order to form further phase images,
   d) determining the amplitude of the excursion of the spins at the fundamental frequency on the basis of the MR phase images,
   e) determining the amplitude of the excursion of the spins at the higher harmonics of the fundamental frequency on the basis of the MR phase images, and
   f) forming an image which is dependent on the ratio of the higher harmonic and fundamental frequency amplitudes.

4. A method as claimed in claim 3, in which the magnetic gradient field (G1, G2) comprises two separate, sinusoidal gradient field oscillations having half the period duration of the mechanical oscillations, the distance in time between said gradient field oscillations amounting to one quarter of the period duration of the mechanical oscillations.

5. A method as claimed in claim 4, in which a refocusing RF pulse acts on the examination zone between the two sinusoidal gradient field oscillations.

6. A method as claimed in claim 3, which method includes the steps of:
   a) additionally calculating the elasticity in the examination zone, and
   b) evaluating the values of distortions and elasticity determined for the same voxel.

7. An arrangement for carrying out the method claimed in claim 2 by means of an MR apparatus, a mechanical oscillation generator, an evaluation unit, a generator which determines the variation in time of magnetic gradient fields, and a control unit which controls the MR apparatus, the generator, the oscillator and the evaluation unit and is programmed in such a manner that the following steps are carried out;
   a) exciting the object by means of temporally periodically, preferably sinusoidally varying mechanical oscillations,
   b) exciting the nuclear magnetization in the object in conjunction with a magnetic gradient field (G1, G2) which is synchronous with the mechanical oscillations, and receiving the MR signals arising in the object in order to form an MR phase image, the variation in time of the gradient field being chosen to be such that the MR signals are determined by excursions at the fundamental frequency as well as by excursions at at least one higher harmonic of the fundamental frequency, c) repeating the step b) a number of times while varying the direction of the gradient of the gradient field and/or the phase difference between the mechanical oscillations and the gradient field in order to form further phase images, d) determining the amplitude of the excursion of the spins at the fundamental frequency on the basis of the MR phase images, e) determining the amplitude of the excursion of the spins at the higher harmonics of the fundamental frequency on the basis of the MR phase images, and f) forming an image which is dependent on the ratio of the amplitudes.

8. A computer media programmed to control an MR apparatus to perform the method as claimed in claim 2.

9. A method as claimed in claim 2, wherein determining the non-linear distortions includes determining a non-linearity coefficient $\alpha$ of Youngs modulus E as expressed by the formula:

$$E = E_0 e^{\alpha \epsilon}$$

where $E_0$ is an initial elasticity and where $\epsilon$ denotes deformation, such that stiffness increases exponentially with increasing deformation.

10. A method as claimed in claim 9 further including determining $E_0$ from the measured variation in time of the excursion.

11. A method as claimed in claim 1 wherein determining the non-linear distortions includes:
   estimating elasatic non-linearity from the measured variations in time of the excursions; and
   applying a Fourier transform to yield a fundamental frequency amplitude and at least one higher frequency amplitude.

12. A method as claimed in claim 2 wherein determining the non-linear distortions includes:
   determining excursion amplitudes at a fundamental frequency and at least at one higher order frequency.

13. A method as claimed in claim 12 further including:
   determining a ratio of the amplitude at the fundamental frequency to the amplitude at the at least one higher order frequency.

14. A computer program for a control unit which acts on an MR apparatus, an oscillation generator and an evaluation unit in order to carry out a method as follows:

a) exciting the object by means of temporally periodically, preferably sinusoidally, varying mechanical oscillations, b) exciting the nuclear magnetization in the object in conjunction with a magnetic gradient field (G1, G2) which is synchronous with the mechanical oscillations, and receiving the MR signals arising in the object in order to form an MR phase image, the variation in time of the gradient field being chosen to be such that the MR signals are determined by excursions at the fundamental frequency as well as by excursions at at least one higher order harmonic of the fundamental frequency, c) repeating the step b) a number of times while varying the direction of the gradient of the gradient field and/or the phase difference between the mechanical oscillations and the gradient field in order to form further MR phase images, d) determining the amplitude of the excursion of the spins at the fundamental frequency on the basis of the MR phase images, e) determining the amplitude of the deflection of the spins at the higher harmonics of the fundamental frequency on the basis of the MR phase images, and f) forming an image which is dependent on the ratio of the amplitude of the at least one higher order harmonic and the amplitude of the fundamental frequency.

* * * * *